(12) United States Patent
Habib et al.

(10) Patent No.: US 6,668,197 B1
(45) Date of Patent: Dec. 23, 2003

(54) TREATMENT USING IMPLANTABLE DEVICES

(75) Inventors: Nagy Adly Habib, London (GB); Alan John Sangster, Scotland (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 09/744,292

(22) PCT Filed: Jul. 22, 1999

(86) PCT No.: PCT/GB99/02393

§ 371 (c)(1), (2), (4) Date: Mar. 27, 2001

(87) PCT Pub. No.: WO00/04946

PCT Pub. Date: Feb. 3, 2000

(30) Foreign Application Priority Data

Jul. 22, 1998 (GB) .............................. 9816012

(51) Int. Cl.[7] .................................. A61N 5/02
(52) U.S. Cl. ........................ 607/101; 607/116
(58) Field of Search ................ 607/101, 103, 607/116, 102; 606/33

(56) References Cited

U.S. PATENT DOCUMENTS

| | | | |
|---|---|---|---|
| 4,397,314 A * | 8/1983 | Vaguine ...................... 607/104 |
| 4,469,098 A | 9/1984 | Davi ...................... 128/303.1 |
| 4,679,561 A * | 7/1987 | Doss ........................... 607/99 |
| 4,719,919 A * | 1/1988 | Marchosky et al. ........ 607/113 |
| 4,825,880 A * | 5/1989 | Stauffer et al. ............. 607/156 |
| 4,974,587 A | 12/1990 | Turner et al. ............... 128/399 |
| 5,190,541 A | 3/1993 | Abele et al. .................. 606/46 |
| 5,369,251 A * | 11/1994 | King et al. .................. 607/116 |
| 5,370,675 A | 12/1994 | Edwards et al. ............ 607/101 |
| 5,472,441 A | 12/1995 | Edwards et al. .............. 604/41 |
| 5,500,012 A | 3/1996 | Brucker et al. ............. 607/122 |
| 5,582,588 A | 12/1996 | Sakurai et al. ................ 604/22 |
| 5,830,139 A | 11/1998 | Abreu ........................ 600/399 |
| 5,833,603 A | 11/1998 | Kovacs et al. .............. 128/630 |
| 5,967,986 A | 10/1999 | Cimochowski et al. ..... 600/454 |
| 5,978,713 A | 11/1999 | Prutchi et al. ................ 607/60 |
| 6,071,281 A | 6/2000 | Burnside et al. ............. 606/41 |
| 6,123,701 A | 9/2000 | Nezhat ........................ 606/33 |
| 6,132,371 A | 10/2000 | Dempsey et al. ........... 600/485 |
| 6,214,032 B1 * | 4/2001 | Loeb et al. ..................... 607/1 |
| 6,231,516 B1 * | 5/2001 | Keilman et al. ............ 600/485 |
| 6,277,114 B1 | 8/2001 | Bullivant et al. ............. 606/41 |
| 6,287,304 B1 | 9/2001 | Eggers et al. ................ 606/37 |
| 6,443,952 B1 | 9/2002 | Mulier et al. ................ 606/49 |

* cited by examiner

Primary Examiner—Lee Cohen
Assistant Examiner—Henry M. Johnson
(74) Attorney, Agent, or Firm—Joel D. Voelzke; Oppenheimer Wolff & Donnelly LLP

(57) ABSTRACT

A method of treatment using implantable devices is disclosed. he method comprises (a) implanting into the body of the human or non-human animal (i) a rectenna capable of receiving electromagnetic radiation in the microwave frequency range and of generating and/or storing electrical energy therefrom, and (ii) an electrically operated therapeutic device arranged to electrical energy from said rectenna; and (b) directing electromagnetic radiation in the microwave frequency range from a source external to the body being treated towards the position of the implanted rectenna so as to genera electrical energy to actuate said therapeutic device.

23 Claims, 3 Drawing Sheets

Schematic of Proposed Interstitial Microwave Array System

SCHEMATIC OF PROPOSED 'WIRELESS' SYSTEM

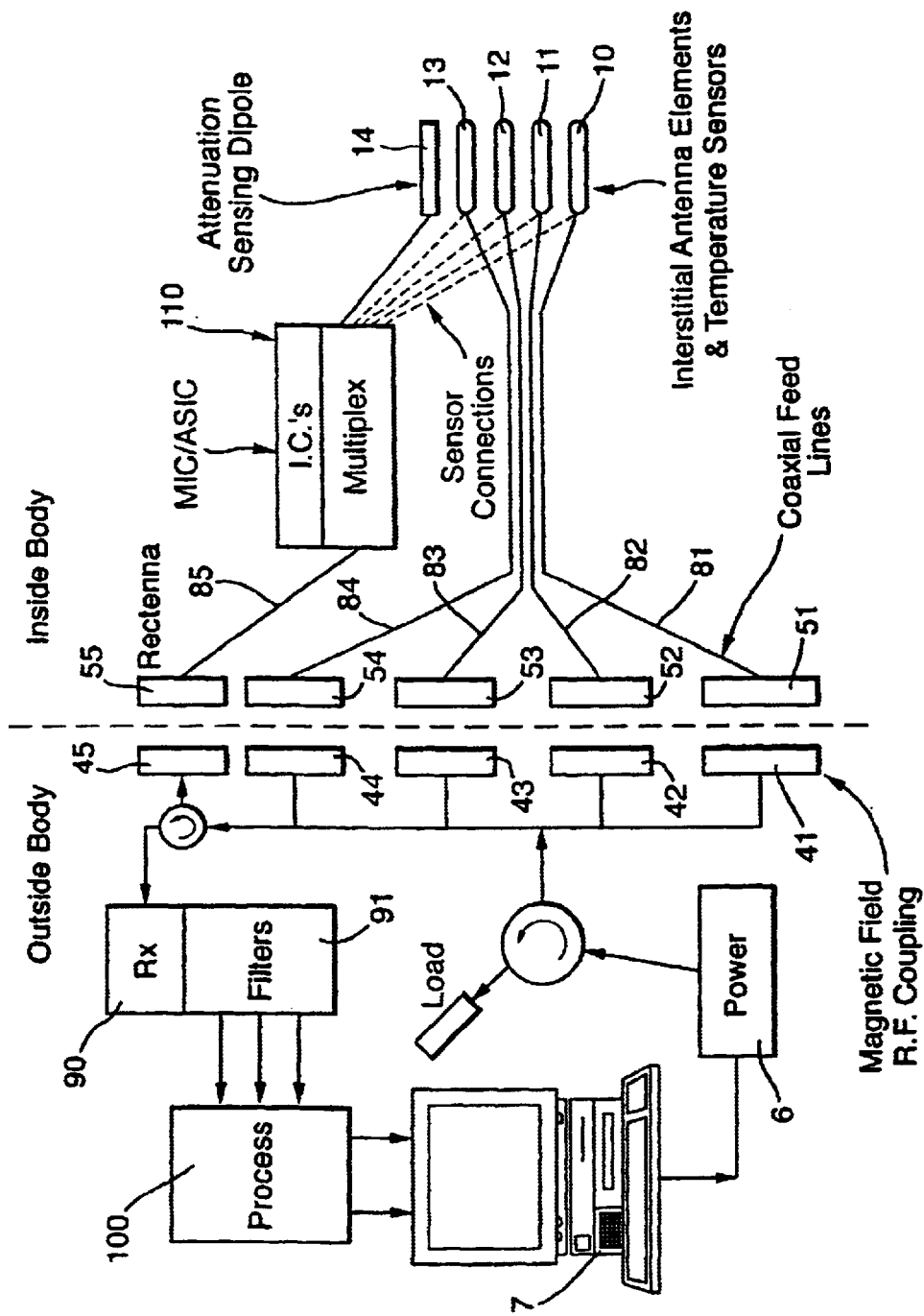

COLONIC STENT

PANCREATIC STENT

TREATMENT USING IMPLANTABLE DEVICES

This invention relates to the treatment of human or non-human animals by means of implantable devices. It is applicable to a variety of treatments but will be described hereinafter with particular reference to hyperthermis treatment, it being understood that the invention is not restricted to this type of treatment Also, the invention will be described on relation to the treatment of human patients, although it is to be understood that the treatments involved may also be applied to non-human animals.

Microwave heating of deep seated tumours has conventionally been achieved by feeding energy from the outside of the body through a small diameter coaxial cable which is terminated in an applicator in the form of a monopole or dipole radiating element. Both the cable and the applicator are inserted close to or within the tumour area either interstitially or through natural orifices into body cavities. In general, the heating pattern is ellipsoidal with the major axis along the applicator axis. Such systems are awkward to use and immobilise the patient. It is therefore desirable to generate an alternative system in which treatment of the patient can be achieved under less distressing conditions and which does not restrict patient mobility.

According to one aspect of the present invention, there is provided a method of performing treatment, e.g. hyperthermia treatment, in a human or non-human animal, which comprises the steps of: (a) implanting into the body of the human or non-human animal (i) a device capable of receiving electromagnetic radiation in the microwave frequency range and of generating and/or storing electrical energy therefrom; and (ii) an electrically operated therapeutic device arranged to receive electrical energy from said device; and (b) directing electromagnetic radiation in the microwave frequency range from a source external to the body being treated towards the position of the implanted device so as to generate electrical energy to actuate said therapeutic device.

According to another aspect of the invention, there is provided apparatus for providing hyperthermis treatment, which comprises a first assembly which, in use, is implanted within the body of the patient and a second assembly which, in use, is located outside the body of the patient, characterised in that:

(A) said first assembly comprises:
  (i) a plurality of antenna elements for the delivery of thermal energy to the site or sites where hyperthermia treatment is to be given;
  (ii) a plurality of inner coupling elements corresponding in number to said antenna elements and each inner coupling element being associated with a given antenna element;
  (iii) an electrical conductor connecting each antenna element with its respective inner coupling element; and (B) said second assembly comprises:
  (i) a plurality of external coupling elements corresponding in number to the inner coupling elements of said first assembly and each external coupling element being associated with a give inner coupling element;
  (ii) a power generating circuit adapted to deliver electromagnetic energy to said external coupling elements; and
  (iii) an electronic control system for controlling the operation of the apparatus, further characterized in that, when the apparatus is in operation:
  (i) each of said external coupling elements is arranged to transmit electromagnetic radiation towards its corresponding inner coupling element, and each of said inner couple elements is arranged to receive electromagnetic radiation; and
  (ii) each of said antenna elements is arranged to covert electromagnetic radiation received by its respective inner coupling element into heat.

Preferably, the implanted device is a rectenna. Further description of the invention will be made with reference to this preferred embodiment.

The rectenna will generally be associated with an implanted electrically operated therapeutic device. Non-limiting examples of the implanted therapeutic device include:

device for delivering heat in a localised manner, e.g. to treat a tumour;

a pump for assisting blood flow;

a stent for ensuring lumen patency of hollow viscars, and ducts, e.g. oesophagus, bile duct, pancreatic duct, colon, stomach, rectum and urethra;

a pressure sensor for detecting localized pressures, e.g. within a stent of the type just mentioned;

a flow meter for determining passage of a fluid through a duct;

a pacemaker;

a detector for a particular chemical or biological material or species, e.g. blood or tissue chemical content or cellular content;

or combinations of such devices.

Typically, these devices require electrical energy for them to function; in some cases, the electrical energy is converted into thermal energy. For example, when used in hyperthermia treatment, the implanted system may comprise a microwave antenna array employing one or more needle-like dipole elements which are implanted into a deep seated tumour. By directing electromagnetic radiation into the tumour, sufficient heat can be generated to kill tumour cells within a defined volume adjacent to the array. Preferably, the implanted array will carry one or more temperature sensors to provide information on temperature build up within the cancer during treatment. The provision of temperature information makes it possible to provide automatic control of the treatment process, ensuring proper administration of microwave energy and overall management of the therapy.

Localised heating can be of benefit in several situations, for example: (a) to stop bleeding, e.g. of a tumour or in a non-malignant condition such as benign ulcers of the stomach or duodenum. The therapeutic device may thus be an electrode or an assembly of electrodes which is activated by the rectenna and generates localised heating of adjacent tissues. An electrode of this sort may, for example, be positioned around a tumour of the prostate, colon, bladder, stomach or lung; it may likewise be positioned adjacent to a duodenal or stomach ulcer.

Other sensors may be incorporated as desired; these can be used, for example, to assess the progress of the treatment.

Alternatively, the implanted system could be a rectenna associated with a metallic stent in, for example, the pancreatic duct of a patient suffering from pancreatic cancer, and the power received by the rectenna is used to heat the stent which in turn transfers heat to the malignant tissues of the organ.

The invention also finds application in surgical procedures involving balloon dilatation and/or coronary stenting.

These surgical procedures tend to encourage the formation of fibrous tissue which can lead to stenosis, e.g. blockage of a blood vessel after removal of the dilatation equipment. In accordance with this invention, such dangers of stenosis may be removed or mitigated by heating the stent during a coronary stenting procedure or by applying heat adjacent to a region undergoing balloon dilatation.

The control of deeply embedded cancers, e.g. within the liver, is problematical. By means of the present invention, it is possible to perform a series of hyperthermia treatments over an extended period of time, thereby providing what is believed to be more effective treatment. In addition, the treatment regimen may be conducted with minimal inconvenience to the patient once the implantation operation has been completed.

An important aspect of the invention is that it enables wireless transmission of electrical energy through transcutaneous tissue at a frequency which is compatible with localised hyperthermia treatment. Currently available systems for transcutaneous transmission of energy generally operate at low frequencies (up to 500 Khz) and are based on inductive coupling between planar coils. Such systems can transfer power levels of up to 40 watts at 70–80% efficiency. These systems, however, are unsuitable for localised hyperthermia treatment which employs microwave applicators because of the need to provide frequency up-conversion within the implanted component of the system; this is an inefficient step which degrades the overall efficiency of the power transfer system. By providing wireless transmission at microwave frequencies, this inefficient step is avoided. For the rectenna element of the system, operating at microwave frequencies means that the available bandwidth for telemetry is vastly improved compared to that available with low frequency coupling systems.

Preferably, the radiation is microwave radiation at a frequency in the range 1–2 Ghz. The implanted receiver is a conveniently placed microwave antenna. Input of radiation to the body is preferably achieved by means of a high frequency magnetic field coupler operating in the region of 1,000–2,000 MHz and designed to carry at least 15 watts power during irradiation treatment. By these means, it is possible to maximise transmission efficiency while minimising tissue heating in the intervening skin layer. The choice of operating frequency will generally be determined by the size of the area to be treated and its depth within the body; the most effective arrangement for deep seated tumours is believed to be to employ needle-like dipole arrays embedded within the tumour and to provide radiation in the microwave range. The needles may be arranged to deliver energy simultaneously or in a predetermined sequence if desired. Another advantage of operating in the microwave frequency range is that sufficient bandwidth is available to permit the same antenna arrangement to be used for telemetry associated with control and monitoring functions.

One embodiment of the magnetic field coupler comprises a rectangular or circular cylindrical resonant cavity operating preferably in its lowest TM mode. One end wall of the resonant cavity coupler typically about 5 mm thick—is inserted under the patient's skin at a depth of about 5 mm. Suitably. aligned coupling apertures are provided in the cavity. By this means, energy can be coupled from the cavity to the antenna feed system. Preferably, each internal needle element of the antenna is supplied with energy through its own coupler.

Advantageously, needle-like dipole antenna elements are used which are 0.5–2.5 cm long and up to 2 mm in diameter. These can deliver thermal energy to deep seated tumours into which they are implanted with relatively high efficiency.

One element of the coupler array may take the form of a rectenna which rectifies the received microwave energy within the body to provide a voltage for the purpose of powering up the implanted electronics and sensors. Multiplexing and coding electronics are preferably included in the system to permit the transfer of sensor information back to the external monitoring system during power up.

For a better understanding of the invention, and to show how the same may be carried into effect, reference will now be made, by way of example, to the accompanying drawings, in which:

FIG. 2 shows more detail of the disposition of implanted components and their operation in hyperthermia treatment of a patient.

Figure 1:
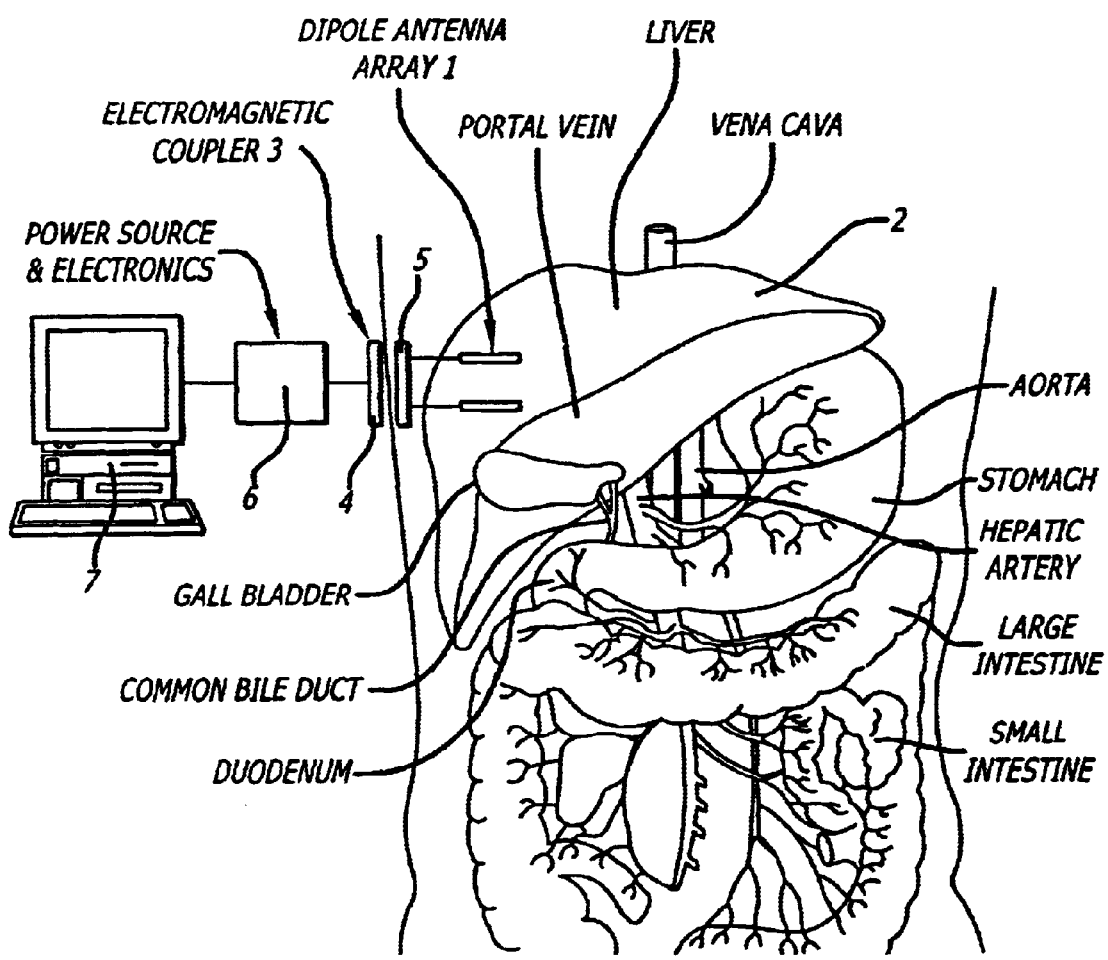
FIG. 1 illustrates schematically the basic power transmission system of this invention.

Referring to FIG. 1, a dipole antenna array 1 is implanted into a malignant region of the liver 2 of a patient. An electromagnetic coupler 3 comprises a first component 4 which, in use, is positioned adjacent the patient's body; and a second component 5 which is implanted within the patient's body at a depth of about 5 mm. Supply of power to external coupler component 4 is achieved by means of electronics system 6 under control of a PC 7.

Referring to FIG. 2, a practical implementation is shown in which there are four interstitial antenna elements 10, 11, 12 and 13 inserted into a tumour within the patient (as illustrated in FIG. 1). Each antenna element is 2 cm long and 1.5 mm in diameter and has associated therewith a temperature sensor element (not shown separately from the antenna element per se). For ease of depiction, the antennae elements are shown as mutually parallel; in fact, they will generally be disposed uniformly about the tumour and will be directed towards the centre of the tumour. This geometry encourages effective heat distribution within the tumour.

Each of the elements 10–13 is connected by conductors 81–84 respectively to its own respective internal coupling element 51–54. Control and power electronics 7 and 6 are illustrated schematically. Rectenna element 55 is connected via line 85 and a multiplexing and coding chip 110 to the sensors at antenna elements 10–13 and to an attenuation sensing dipole 14.

Each of the internal coupling elements 51–55 functions in conjunction with external coupling elements 41–45, respectively. Element 45 is connected to a receiver 90 which includes filters 91 and is operatively connected to a process control system 100 which in turn is operatively connected to the PC 7.

Also implanted within the patient is a transceiver 110 which is operatively connected, on the one hand, to the temperature sensors of elements 10–13 and to attenuation sensing dipole 14; and, on the other hand, to the coupling elements 51–55.

By means of a system as just described, it may be possible to provide relatively simple, auto-regulated control of tumours which, because of their siting or their characteristics or the previous treatment history of the patient are not susceptible to conventional methods of treatment.

The system as described may be used in conjunction with secondary techniques, for example the direct injection of paracrine hormones or of cells secreting paracrine hormones. These are believed to promote apoptosis of tumours and/or to encourage infiltration of the heated tumour by cells of the innate immune system.

In designing the components for implantation in the present invention, it is desirable to minimise the size of the components to reduce tissue damage during the implantation step; to maximise their rigidity to increase the accuracy with which they can be positioned within the body of a patient; and to encapsulate the components in non-toxic, non-reactive material. Further, the control system employed preferably allows different modes of activation of the antenna elements 10–13 so as to permit variation of the spatio-temporal heat delivery.

Figure 3A:
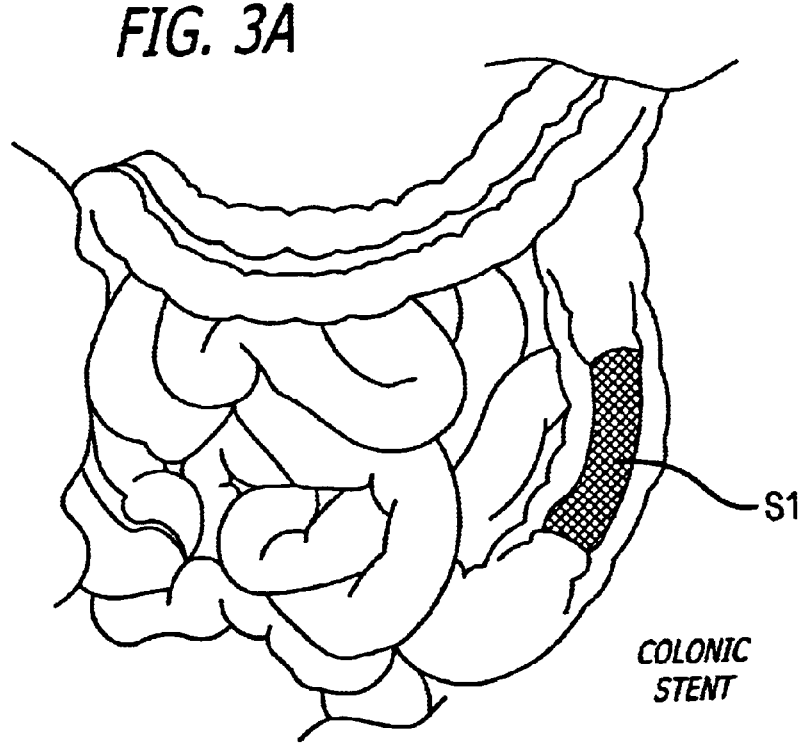
FIGS. 3A and 3B illustrate stents implanted, respectively, in the colon and in the pancreatic duct.
Figure 3B:
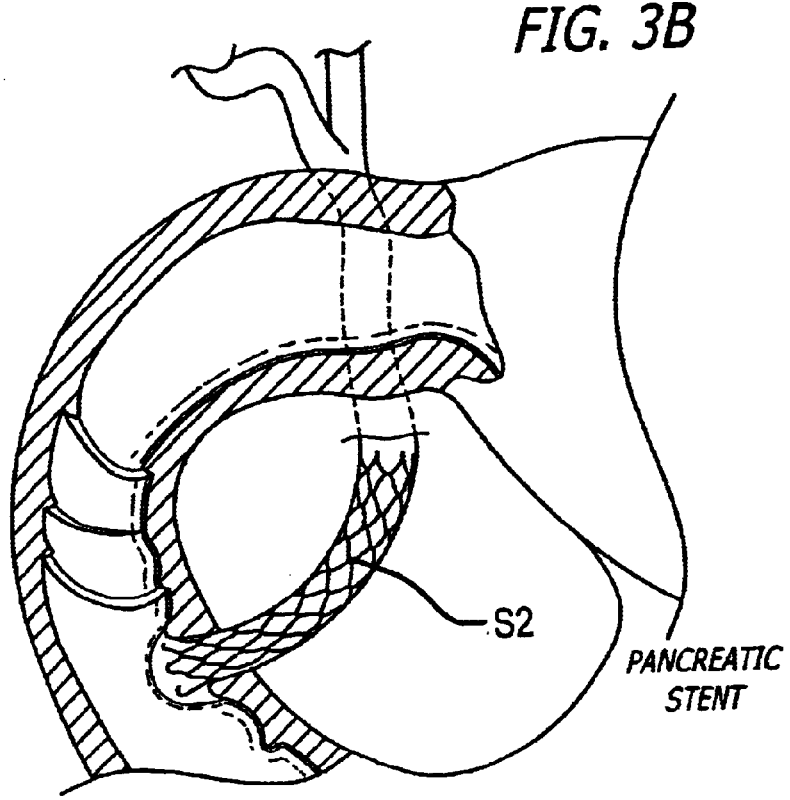

FIGS. 3A and 3B show metallic or metal-containing stents $S_1$ and $S_2$. respectively, in the human colon and pancreatic duct. These serve to maintain the lumen patency of the organs or ducts in which they are implanted, and where partial or complete occlusion (e.g. by a tumour) has occurred. By implanting coupling elements and a rectenna in operative connection with the stent, heat may be delivered to kill the tumour cells. As illustrated in FIG. 2, control and monitoring means may be incorporated to provide telemetric control and operation of the hyperthermia treatment.

What is claimed is:

1. A method of performing hyperthermia treatment, in a human or non-human animal, which comprises the steps of:
   (a) implanting into the body of the human or non-human animal
      (i) a receiving device capable of receiving electromagnetic radiation in the microwave frequency range of 1–2 GHz and of generating and/or storing electrical energy therefrom; and
      (ii) an electronically operated therapeutic device arranged to receive electrical energy from said receiving device; and
   (b) directing electromagnetic radiation in the microwave frequency range of 1–2 GHz from a source external to the body being treated towards the implanted receiving device so as to generate electrical energy to actuate said therapeutic device.

2. A method as claimed in claim 1, characterized in that said receiving device is a rectenna.

3. A method as claimed in claim 1, characterized in that said electronically operated therapeutic device is at least one of:
   (1) a device for delivering heat in a localized manner;
   (2) a pump for assisting blood flow;
   (3) a stent for ensuring lumen patency of hollow viscera and ducts;
   (4) a pressure sensor for detecting localized pressures;
   (5) a flow meter for determining passage of a fluid through a duct;
   (6) a drug release device;
   (7) a pacemaker; or
   (8) a detector for a particular chemical or biological material or species.

4. A method as claimed in claim 3, characterized in that said therapeutic device comprises one or more needle-like dipole elements for implanting into a tumor.

5. A method as claimed in claim 3, characterized in that said therapeutic device comprises an electrode or an assembly of electrodes adapted to heat adjacent tissues.

6. A method as claimed in claim 5, characterized in that said electrode or assembly of electrodes is positioned around a tumor.

7. A method as claimed in claim 3, characterized in that said therapeutic device comprises a stent which is arranged to be heated.

8. A method as claimed in claim 1, characterized in that input of radiation to the body is achieved by means of a magnetic field coupler operating in the region of 1–2 GHz.

9. A method as claimed in claim 8, characterized in that said magnetic field coupler is designed to carry at least 15 watts power during irradiation treatment.

10. An apparatus for providing hyperthermia treatment, which comprises a first assembly which, in use, is implanted within a human or non-human body and a second assembly which, in use, is located outside the body, characterized in that:
   (a) said first assembly comprises:
      (i) a plurality of antenna elements for the delivery of thermal energy to a site or sites where hyperthermia treatment is to be given;
      (ii) a plurality of inner coupling elements corresponding in number to said antenna elements and each inner coupling element being associated with a given antenna element;
      (iii) an electrical conductor connecting each antenna element with its respective inner coupling element; and
   (b) said second assembly comprises:
      (i) a plurality of external coupling elements corresponding in number to the inner coupling elements of said first assembly and each external coupling element being associated with a given inner coupling element;
      (ii) a power generating circuit adapted to deliver electromagnetic energy to said external coupling elements; and
      (iii) an electronic control system for controlling the operation of the apparatus, wherein, when the apparatus is in operation:
         (i) each of said external coupling elements is arranged to transmit electromagnetic radiation towards its corresponding inner coupling element, and each of said inner coupling elements is arranged to receive electromagnetic radiation; and
         (ii) each of said antenna elements is arranged to convert electromagnetic radiation received by its respective inner coupling element into heat.

11. Apparatus as claimed in claim 10, characterized in that the apparatus is arranged to allow different modes of activation of the individual antenna elements so as to permit variation of the spatio-temporal heat delivery.

12. Apparatus as claimed in claim 10, characterized in that said antenna elements are, in use, arranged to deliver thermal energy to a stent.

13. Apparatus as claimed in claim 10, further characterized in that said electromagnetic radiation is microwave radiation.

14. Apparatus as claimed in claim 13, characterized in that said microwave radiation has a frequency in the range 1–2 GHz.

15. A set of devices for implantation into the body of a human or non-human animal, which set comprises:
   (a) a receiving device capable of receiving electromagnetic radiation in the microwave frequency range of 1–2 GHz and of generating and/or storing electrical energy therefrom, and
   (b) an electrically operated therapeutic device arranged to receive electrical energy from said receiving device.

16. The set of devices of claim 15, characterized in that the said receiving device is a rectenna.

17. The set of devices of claim 15, characterized in that said electrically operated therapeutic device is at least one of:
   (1) a device for delivering heat in a localized manner;
   (2) a pump for assisting blood flow;
   (3) a stent for ensuring lumen patency of hollow viscera and ducts;
   (4) a pressure sensor for detecting localized pressures;
   (5) a flow meter for determining passage of a fluid through a duct;
   (6) a drug release device;
   (7) a pacemaker; or
   (8) a detector for particular chemical or biological materials or species.

18. A set of devices as claimed in claim 17, characterized in that said therapeutic device comprises one or more needle-like dipole elements for implanting into a tumor.

19. A set of devices as claimed in claim 17, characterized in that said therapeutic device comprises an electrode or an assembly of electrodes adapted to heat adjacent tissues.

20. A set of devices as claimed in claim 19, characterized in that said electrode or assembly of electrodes is positioned around a tumor.

21. A set of devices as claimed in claim 17, characterized in that said therapeutic device comprises a stent which is arranged to be heated.

22. A set of devices as claimed in claim 15, characterized in that input of radiation to the body is achieved by means of a magnetic field coupler.

23. A set of devices as claimed in claim 22, characterized in that said magnetic field coupler is designed to carry at least 15 watts power during irradiation treatment.

* * * * *